(12) United States Patent
Blaha et al.

(10) Patent No.: US 7,528,094 B2
(45) Date of Patent: May 5, 2009

(54) METHOD AND APPARATUS FOR PROVIDING SAFE LONG-RANGE TELEMETRY WITH IMPLANTABLE MEDICAL DEVICES

(75) Inventors: Eric V. Blaha, Hudson, WI (US); James H. Ericksen, North Oaks, MN (US); Dean A. Hooper, Oak Grove, MN (US); Javaid Masoud, Shoreview, MN (US); James A. Zimmerman, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 203 days.

(21) Appl. No.: 10/972,638

(22) Filed: Oct. 25, 2004

(65) Prior Publication Data
US 2006/0089684 A1 Apr. 27, 2006

(51) Int. Cl.
*A61N 1/00* (2006.01)
(52) U.S. Cl. .......................................... 507/60; 607/32
(58) Field of Classification Search ................... 607/30, 607/32, 60, 65, 31; 128/903; 600/302
See application file for complete search history.

(56) References Cited

U.S. PATENT DOCUMENTS

| | | | |
|---|---|---|---|
| 4,550,370 A | 10/1985 | Baker | |
| 5,755,737 A * | 5/1998 | Prieve et al. | 607/4 |
| 5,843,139 A * | 12/1998 | Goedeke et al. | 607/32 |
| 6,169,925 B1 | 1/2001 | Villaseca et al. | |
| 6,240,317 B1 | 5/2001 | Villaseca et al. | |
| 6,250,309 B1 | 6/2001 | Krichen et al. | |
| 6,418,346 B1 | 7/2002 | Nelson et al. | |
| 6,442,433 B1 | 8/2002 | Lindberg | |
| 6,480,745 B2 | 11/2002 | Nelson et al. | |
| 6,482,154 B1 * | 11/2002 | Haubrich et al. | 600/300 |
| 6,574,511 B2 | 6/2003 | Lee | |
| 6,599,250 B2 | 7/2003 | Webb et al. | |
| 6,600,952 B1 * | 7/2003 | Snell et al. | 607/31 |
| 6,985,773 B2 * | 1/2006 | Von Arx et al. | 607/32 |
| 2003/0149459 A1 * | 8/2003 | Von Arx et al. | 607/60 |
| 2004/0260363 A1 * | 12/2004 | Arx et al. | 607/60 |
| 2005/0113885 A1 * | 5/2005 | Haubrich et al. | 607/60 |
| 2006/0030901 A1 * | 2/2006 | Quiles et al. | 607/60 |

* cited by examiner

*Primary Examiner*—Carl H Layno
*Assistant Examiner*—Brian T Gedeon

(57) ABSTRACT

An implantable medical device (IMD) communication system and associated method for controlling the telemetry link status between an IMD and associated programmer during a telemetry session are provided. The system includes control circuitry for detecting conditions during predetermined time intervals for determining if a telemetry session is active or inactive. If a telemetry session is determined to be inactive for a specified interval of time, the telemetry link may be terminated or converted to a low-output, stand-by mode. Patient or device identity verification may be required prior to allowing programmer-IMD communication. A patient alert signal may be generated in response to programmer-IMD communication occurring after a predetermined time of telemetry session inactivity.

23 Claims, 9 Drawing Sheets

METHOD AND APPARATUS FOR PROVIDING SAFE LONG-RANGE TELEMETRY WITH IMPLANTABLE MEDICAL DEVICES

FIELD OF THE INVENTION

The present invention relates generally to implantable medical device (IMD) telemetry systems and more particularly to a system and associated method for automatically controlling a telemetry link status during a telemetry session.

BACKGROUND OF THE INVENTION

A variety of programmable implantable medical devices are available which typically utilize radio frequency (RF) telemetry for communicating with an external programmer. Such devices include cardiac pacemakers and defibrillators, drug pumps, neuromuscular stimulators, hemodynamic monitors and other physiological monitors. Programming commands or data are transmitted between an implanted RF telemetry antenna and associated circuitry and an external RF telemetry antenna associated with the external programmer. In the past, the external RF telemetry antenna has been contained in a programmer RF head so that it can be located close to the patient's skin overlying the IMD. Programmer RF heads are well known in the art. See for example U.S Pat. No. 4,550,370 issued to Baker, incorporated herein by reference in its entirety. Such telemetry systems may be referred to as "near-field" systems because they require the external antenna to be positioned in close proximity to the implanted antenna in order to establish and maintain telemetry communication.

Long range or far-field telemetry systems have been introduced wherein the external telemetry antenna may be located a distance away from the patient, for example a few meters or so from the patient, during telemetry communication. The external RF telemetry antenna can be located on the case of the programmer or otherwise integrated with the programmer or an associated stand or cart. Such long-range telemetry systems are generally preferable over systems requiring an RF head because it frees the hands of the clinician for performing other tasks during an interrogation or programming session. Moreover, the patient may be active, e.g., performing treadmill or other exercise or stress testing, during a telemetry transmission. Telemetry systems that do not require the use of a programmer RF head are generally disclosed in U.S. Pat. No. 6,240,317 issued to Villaseca et al., U.S. Pat. No. 6,169,925 Villaseca et al., and U.S. Pat. No. 6,482,154 Haubrich et al., all of which patents are incorporated herein by reference in their entirety.

One issue may arise with the use of long-range telemetry systems when the clinician completes a programming procedure and the patient walks away from the programmer but remains within telemetry range of the programmer. An established telemetry session may be maintained between the programmer and the patient's IMD unbeknownst to the patient or clinician. Unintentional programming or interrogation of the IMD may occur as long as the telemetry link is maintained. The clinician may begin a new programming session with a new patient and inadvertently interrogate or program the previous patient's IMD thinking a telemetry link is established with the IMD of the new patient. Another person, unqualified to perform programming operations, may inadvertently program a device that remains within telemetry range of the programmer.

Another disadvantage of an unintentionally sustained telemetry session is unnecessary battery consumption in the IMD. As long as the telemetry link is maintained, the IMD telemetry circuitry will consume battery power in a high-output mode. If the patient remains within the communication range of a programmer after programming and interrogation procedures are completed, IMD battery power is unnecessarily consumed in maintaining the high-output communication link. In past practice, the use of a programming RF head terminated a telemetry link upon removal of the RF head from a position over the implanted device. With the development of long-range telemetry systems, a method is needed for preventing unintentional communication with an IMD and unnecessary IMD battery consumption due to sustained long-range telemetry communication between an IMD and a programmer.

BRIEF SUMMARY OF THE INVENTION

The present invention provides a long-range telemetry system and associated method for controlling the telemetry link status during a telemetry session. The system includes a programmer equipped with telemetry circuitry adapted for bidirectional communication with an IMD. The programmer includes control circuitry, typically in the form of a microprocessor, for controlling programming and interrogation functions of the programmer. The IMD includes telemetry circuitry for communicating with the programmer and control circuitry for controlling IMD operations, which can include therapy delivery and/or monitoring functions. The associated method for controlling the telemetry link status during a telemetry session may be operated under the control of the IMD control circuitry, the programmer control circuitry or a combination of both.

In one embodiment of the associated method, control circuitry monitors for one or more conditions used to verify that a telemetry session is active. If active telemetry conditions are not detected for a predetermined interval of time, operations to terminate the high-output telemetry link are initiated.

In another embodiment, after the first predetermined time interval expires without detection of active telemetry session conditions, the control circuitry monitors for a second set of conditions used to verify that the telemetry session is inactive. If the second set of conditions is detected for a predetermined second interval of time, operations to terminate the high-output telemetry link are initiated.

Operations for terminating the high-output telemetry link may include terminating the link when a telemetry session is determined to be inactive and putting the IMD telemetry circuitry to sleep. Alternatively, telemetry link termination operations may include setting a timer to a specified time interval during which a user-notification message may be displayed alerting the user that the link is about to be terminated. Upon expiration of the time interval, the high-output telemetry link is terminated. Prior to expiration of the time interval, the user may have the option to continue the telemetry session and thereby cancel the telemetry termination operation.

In yet another embodiment, the telemetry termination operation includes terminating the high-output telemetry link by putting the IMD telemetry circuitry into a low-output, stand-by mode. In order to restore the high-output telemetry link, the patient and/or device identity may require verification by a user such that the telemetry session is continued with the intended patient.

In another embodiment, if criteria for detecting an inactive telemetry session have been satisfied for a predetermined interval of time, verification of the intended patient and/or device identity is required before the programmer will respond to a user-entered command or request. The telemetry link status may remain in a high-output mode if the correct identity is confirmed. If the identity of the patient and/or device that the programmer is communicating with is not confirmed as the intended device, the telemetry link may be terminated, automatically or manually.

DETAILED DESCRIPTION OF THE PREFERRED EMBODIMENTS

Figure 1:
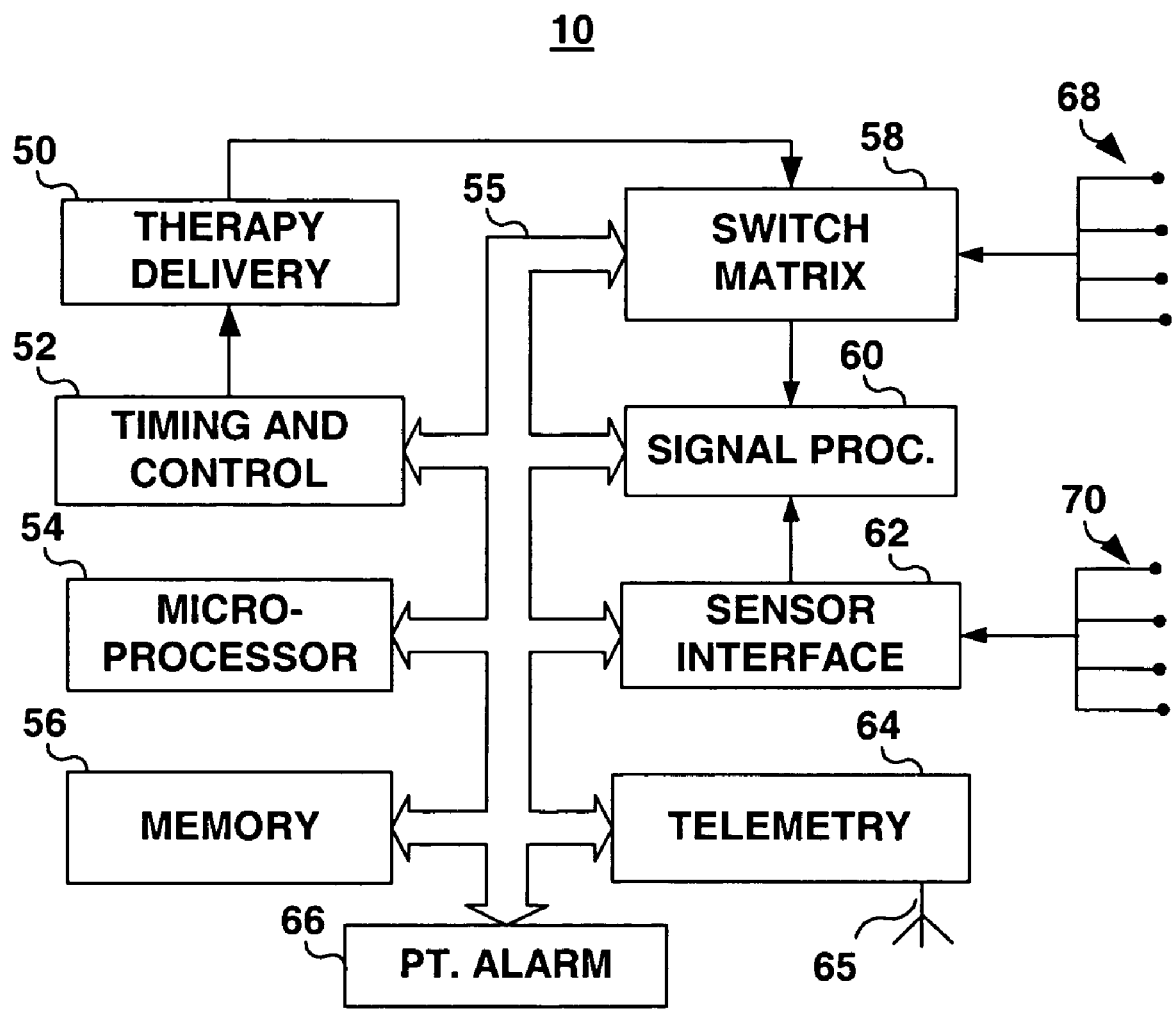
FIG. 1 is a block diagram of typical functional components of an IMD.

FIG. 1 is a block diagram of typical functional components of an IMD. IMD 10 generally includes timing and control circuitry 52 and an operating system that may employ microprocessor 54 or a digital state machine for timing and controlling sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control unit 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses. In other embodiments, electrodes 68 may be used for measuring impedance signals for monitoring, for example, edema, respiration or heart chamber volume.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological data may be recorded continuously by IMD 10 or upon a detected triggering event or change in a monitored physiological condition. Acquired physiological data may be stored for later transfer to an external programmer or monitor or transferred in real-time.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. Microprocessor 54 controls device diagnostic functions, such as lead impedance monitoring, stimulation threshold testing, and device longevity estimation. Microprocessor 54 may also manage the storage of device performance parameters such as pacing capture success rate, frequency of delivered therapies, and response to delivered therapies. Device-related parameters acquired by IMD 10 may be transferred to an external programmer for evaluating device function.

Microprocessor 54 may be programmed to generate an alert or alarm notifications in response to detecting predetermined physiological or device-related conditions or events. A patient alert signal is generated by patient alarm circuitry 66. A patient alert signal may be an audible sound or a perceivable vibration or other sensory stimulation. In accordance with the present invention, a patient alert signal may be generated if telemetry communication is attempted after a predetermined period of inactivity following a telemetry session.

IMD 10 is equipped with telemetry circuitry 64 and antenna 65 for bidirectional communication with an external programmer. Programming data and monitoring data are transmitted during downlink or uplink telemetry between IMD telemetry circuitry and external telemetry circuitry included in the programmer. In an exemplary embodiment, telemetry circuitry 64 and antenna 65 are implemented as a long range telemetry system which allows IMD-to-programmer communication to occur without user intervention, e.g. without the use of a programming head. Communication between IMD 10 and an external programmer may occur while the patient moves freely within the telemetry range of the external telemetry circuitry.

Figure 2:
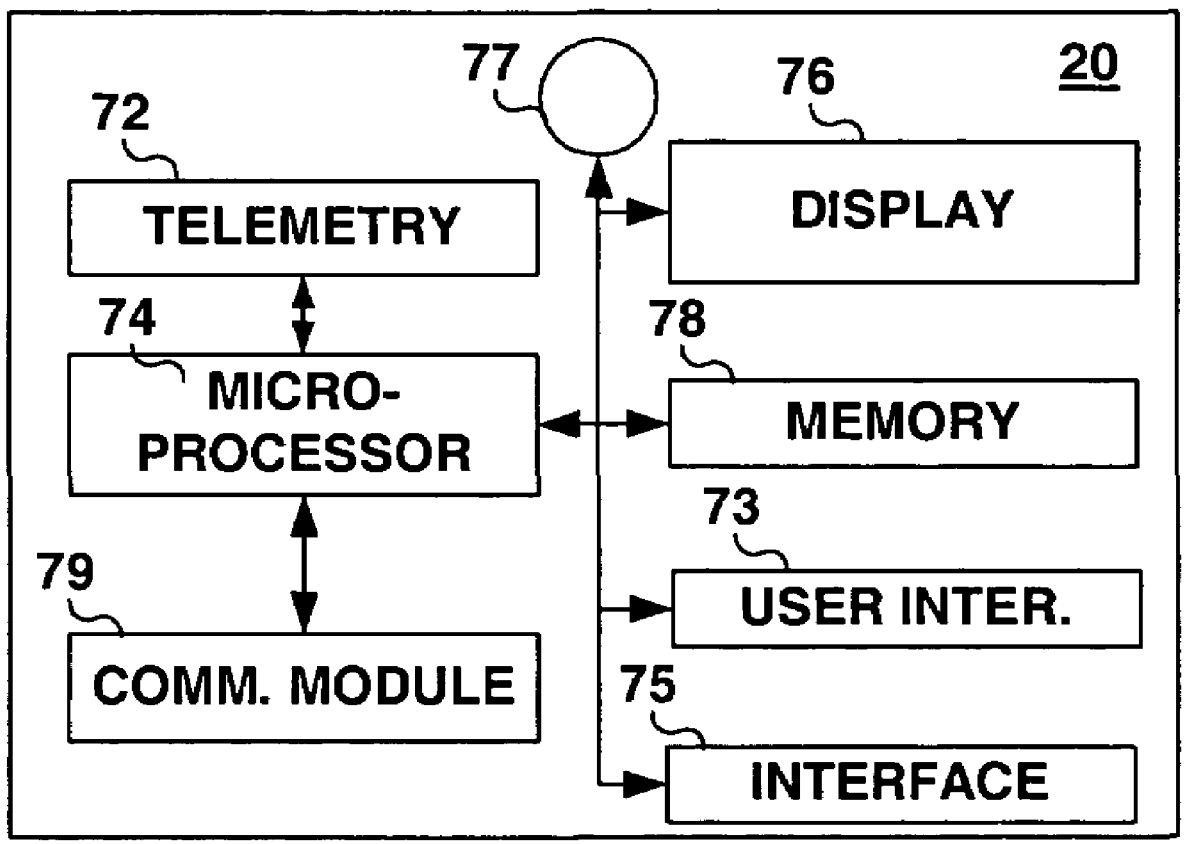
FIG. 2 is a functional block diagram of typical components included in an external programmer.

FIG. 2 is a functional block diagram of typical components included in an external programmer. In one method for practicing the present invention, programmer 20 is located in a clinic or other medical facility and used for interrogating and programming IMDs for multiple patients. Automatic control of telemetry link status between programmer 20 and an IMD reduces the likelihood of inadvertent programming or interrogation of the IMD. Aspects of the present invention for automatically controlling the status of a telemetry link may be incorporated in any system used for communicating with an IMD such as systems including a home monitor, patient programmer, or other external device enabled for programming or interrogating an IMD. The use of the term "programmer" herein is therefore not intended to be limiting to a particular type of external device but refers generally to any external device enabled to establish a communication link with an IMD and with which automatic control of telemetry link status is desired.

Programmer 20 shown in FIG. 2 includes a telemetry circuit 72 for bidirectional communication with an IMD, such as IMD 10 shown in FIG. 1. Programmer 20 may be a microprocessor-controlled device wherein microprocessor 74 operates with associated memory 78 for controlling programmer functions, including automatic telemetry link status control in accordance with the present invention.

Memory 78 is used alone or in combination with IMD memory 56 (FIG. 1) to store information used in telemetry link control operations. Such information may include conditions for verifying a telemetry session is active or inactive, time intervals for monitoring for such conditions, and messages that may be displayed during a telemetry termination operation. Parameters used in controlling telemetry link status may be fixed values stored in memory 78 (and/or IMD memory) or customized values programmable by a clinician using user interface 73.

In order for the clinician to interact with programmer 20, a keyboard, graphical user interface, or other user interface 73, coupled to microprocessor 74, is provided. Display 76 and/or the user interface 73 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems.

Display 24 is used to display patient related data, menu choices and data entry fields used for entering data during a telemetry session. Display screen 24 also displays a variety of screens of retrieved IMD data, previously stored or in real time and may display uplinked event signals as they are received and thereby serve as a means for enabling the user to timely review IMD operating history and status. Display 76 is used for displaying messages to a user regarding telemetry link status during the telemetry link control operations provided by the present invention. A speaker 77 may also be provided for broadcasting audible tones or messages used to alert the user to telemetry, programming, and/or interrogation status or conditions.

Programmer 20 may include a communications module 79, which may be embodied as a modem, used for transferring data to a central database or communicating with other patient management systems. Programmer 20 may further include an interface 75 for coupling peripheral devices which may include external monitoring equipment such as ECG leads, blood pressure monitor, etc.

Figure 3A:
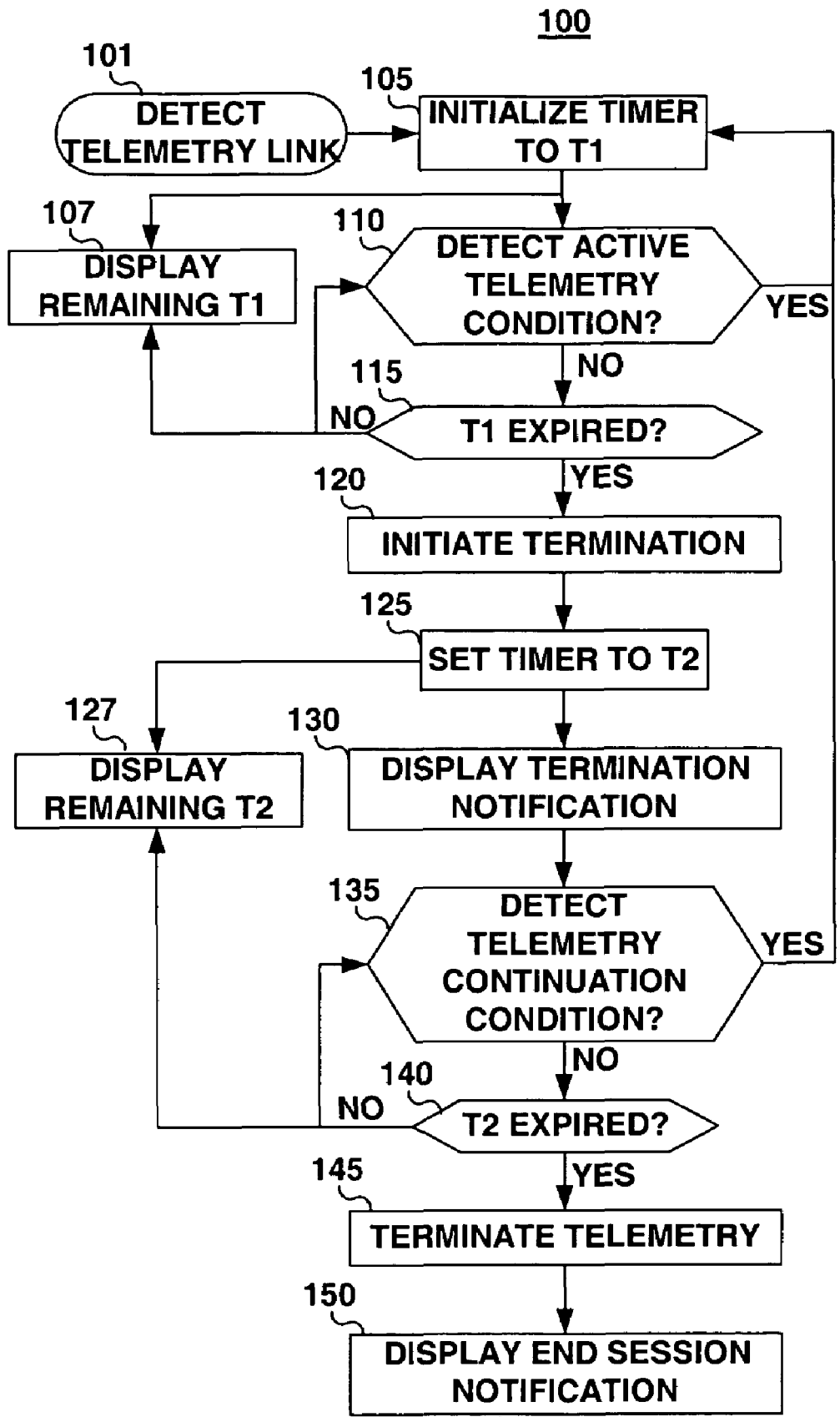
FIG. 3A is a flow chart summarizing steps included in a method for automatically terminating a telemetry session.

FIG. 3A is a flow chart summarizing steps included in a method for automatically terminating a telemetry session. Steps included in method 100 may be implemented in the control circuitry of a programmer, such as programmer 20 shown in FIG. 2, in the control circuitry of an IMD, such as IMD 10 shown in FIG. 1, or a combination of a programmer and IMD control circuitry.

At initiation step 101, an established telemetry link between an IMD and programmer is detected, marking the beginning of a new telemetry session. A telemetry session, as referred to herein, begins upon establishment of a telemetry link and extends as long as the telemetry link is maintained. A telemetry session may include multiple programming and interrogation operations. At step 105, a timer is initialized to a first time interval, T1, during which conditions or events are monitored for verifying that the new telemetry session is active as indicated by step 110.

Conditions or events indicating that a telemetry session is active may include any user input to the programmer, data transmission between the IMD and programmer, detection of a near field signal such as a magnet or programming head, or the presence of ECG signal input or other external monitoring signal input coupled to the programmer interface. Each time an active telemetry condition is detected, as determined at decision step 110, method 100 returns to step 105 to reset a timer to T1.

At the same time active telemetry conditions are being monitored at step 110, the time remaining in T1 may optionally be displayed by the programmer at step 107. Remaining time in the T1 interval may be displayed continuously or at set intervals so that a user is aware when the current telemetry session will be determined inactive if no active telemetry conditions are detected.

If T1 expires, as determined at decision step 115, before an active telemetry condition is detected, an automatic telemetry termination operation is initiated at step 120. In some embodiments, termination of a telemetry session may occur upon the expiration of T1 with no further action or warning. The telemetry link is terminated, and the IMD telemetry circuitry is put to sleep.

In an exemplary embodiment and as shown in FIG. 3A, the telemetry termination operation begins at step 125 by setting a timer to a second time interval T2. A termination notification message may be displayed by the programmer at step 130. A user may respond to the termination notification message within the second time interval T2 to cause the termination operation to be aborted. A user's response may be a continuation command entry or other predefined telemetry continuation condition. Conditions monitored during the first time interval T1 for verifying an active telemetry session may also be monitored during the second time interval T2 for detecting a continuation condition. The time remaining in the T2 time interval may optionally be displayed at step 127 while continuation conditions are being monitored.

If a telemetry continuation condition is detected at decision step 135, method 100 returns to step 105 to reset a timer to T1 and continue monitoring for active telemetry conditions. If the second time interval T2 expires, as determined at decision step 140, without detection of a telemetry continuation condition, automatic termination of the telemetry link is executed at step 145. A message may be displayed on the programmer at step 150 notifying the user that the telemetry session has ended.

The time intervals T1 and T2 may be the same or different durations. In one embodiment, T1 may be set to a relatively longer duration, for example one to ten minutes, and T2 may be set to a shorter duration, for example 30 to 60 seconds. These intervals may be fixed parameters or user programmable. T1 and T2 may be set according to the telemetry session scenario, for example if the telemetry session is occurring during an implantation procedure versus a follow-up procedure, different time intervals during which telemetry session activity is monitored may be desirable. Time remaining in either or both time intervals may be displayed by the programmer.

Figure 3B:
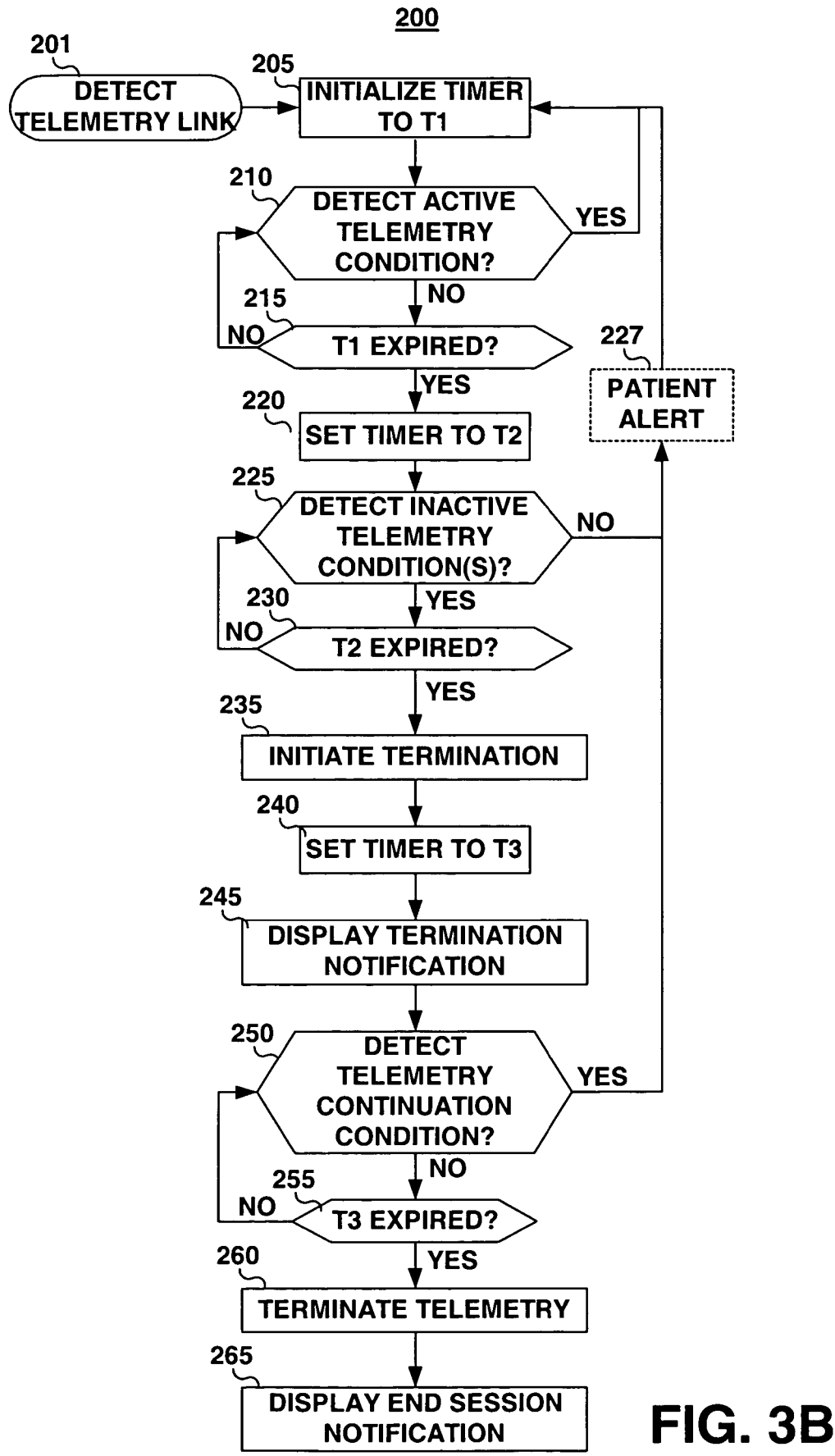
FIG. 3B is a flow chart summarizing steps included in an alternative method for automatically terminating a telemetry session.

FIG. 3B is a flow chart summarizing steps included in an alternative method for automatically terminating a telemetry session. After detecting the establishment of a new telemetry link at step 201, a timer is initialized to a time interval T1 at step 205 during which method 200 monitors for conditions of active telemetry at step 210. The time remaining in T1 may be displayed by the programmer as described in conjunction with FIG. 3A. Upon expiration of T1 without detection of an active telemetry session condition, a second timer is set to a time interval T1' at step 220. During the time interval T1', method 200 monitors for conditions indicating the telemetry session is inactive. Such conditions may include the absence of user input to the programmer, the absence of data transmissions between the programmer and IMD, the removal of a near-field signal such as a magnet or programming head, or the loss of an external monitoring signal such as an ECG or blood pressure signal. Detection of the patient moving out of the telemetry range of the programmer may also be an inactive telemetry condition. Movement out of the telemetry range may be detected using an activity sensor in the IMD that would indicate patient movement or using a received signal strength indicator implemented in the programmer.

A set of conditions evidencing an inactive telemetry session may all be required to be detected in order to determine the telemetry session is inactive. If any one condition is not detected, the session may still be active. On the contrary, any one condition evidencing an active telemetry session during the first time interval T1 may be adequate to verify a telemetry session is active.

If inactive telemetry conditions are not detected at decision step 225, the telemetry session is determined to be active again. Method 200 may return to step 205 to reinitialize a timer to T1. A patient alert signal may be generated at optional step 227 to alert a patient that a telemetry session is still active. An attempt by the programmer to communicate with the IMD after a period of inactivity may cause the IMD to generate a patient alert. In particular, an attempt to transfer a programming or interrogation command from the programmer to the IMD may cause the IMD to generate a patient alert signal to notify the patient that a programming or interrogation operation is being attempted. In other embodiments, a patient alert signal may occur in response to specified programmer-IMD communications that occur after any designated period of inactivity following an active telemetry session. In one example, the generation of a patient alert signal may be limited to occur in response to certain types of communication such as programming of operating parameters deemed critical to patient safety.

In an alternative embodiment, if inactive telemetry conditions are not detected at decision step 225, method 200 may return to step 220 to reinitialize the timer to T1'. Monitoring for inactive telemetry conditions would continue until T1' expires.

If inactive telemetry conditions are detected at decision step 225, and the second time interval T1' is expired, as determined at decision step 230, the telemetry termination operation is initiated at step 235. The telemetry termination operation may include a single step of terminating the telemetry link upon expiration of T1'. Alternatively, the termination operation may include step 240 for setting a timer to a third time interval T2 and displaying a pending termination notification message on the programmer at step 245. If a telemetry continuation condition is detected at step 250, method 200 returns to step 205 to reset a timer to T1 and monitor for active telemetry conditions. A telemetry continuation condition may be a "continue" command entered by a user prior to expiration of the T2 time interval. Time remaining in the T1' time interval may be displayed by the programmer while monitoring for inactive telemetry conditions and time remaining in the T2 time interval may be displayed while monitoring for continuation conditions.

If no telemetry continuation conditions are detected before the interval T2 expires, as determined at decision steps 250 and 255 respectively, the telemetry session is terminated at step 260. A message may be displayed on the programmer at step 265 indicating the telemetry session has ended.

Figure 4:
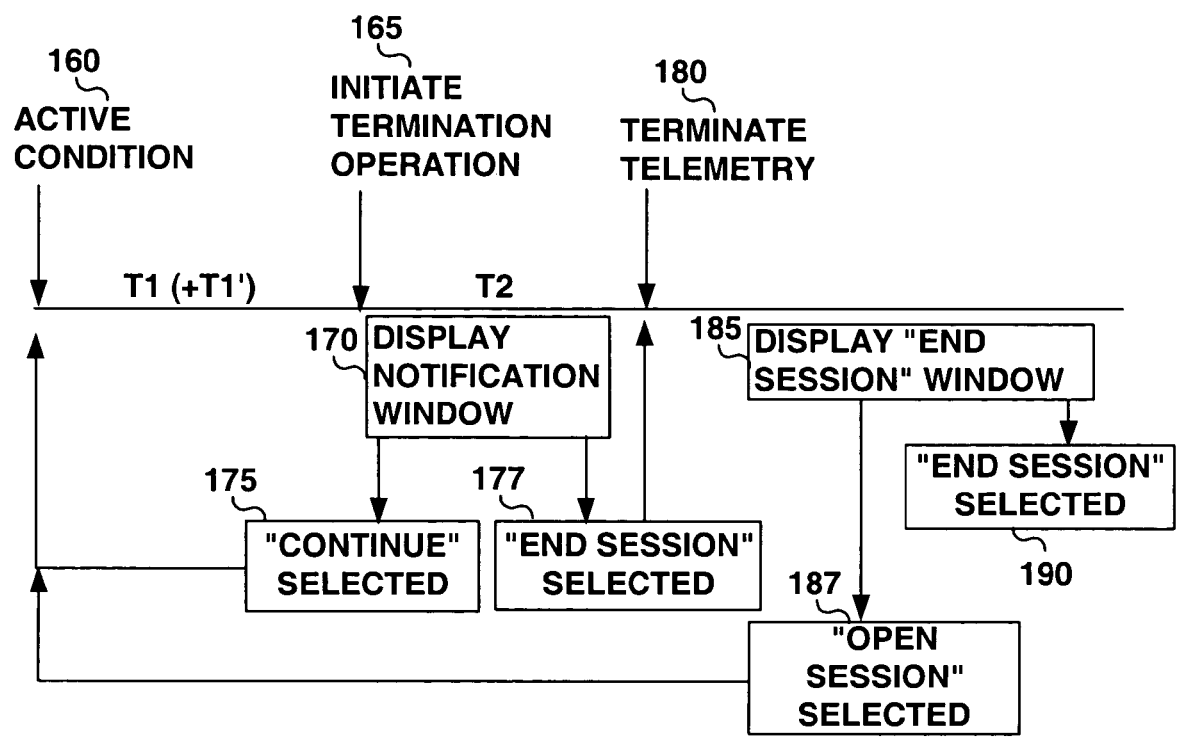
FIG. 4 is a timeline summarizing events that may occur during a telemetry session including automatic telemetry termination methods.

FIG. 4 is a timeline summarizing events that may occur during a telemetry session including automatic telemetry termination methods. Detection of an active telemetry condition at 160 sets a timer to T1. After a period of inactivity (which may include an interval T1' in accordance with method 200 of FIG. 3B), a telemetry termination operation is initiated at 165. A window is displayed on the programmer at 170 notifying the user that the telemetry session will be terminated after a time interval T2.

The notification window 170 may include a "continue session" field for selection by a user in order to abort the termination operation and continue the telemetry session. If the "continue session" field is selected by a user at 175, the timer is reset to T1 and the timeline starts over. The notification window displayed at 170 may further include an "end session" field to allow the user to confirm that the session may be ended. If the "end session" field is selected at 177, or the time interval T2 expires, the telemetry link is terminated at 180.

Upon terminating the telemetry link, a window is displayed at 185 indicating that the telemetry session is ended. The end telemetry window may include an "open session" field for selection by a user to re-establish the telemetry session with the same patient. If the "open session" field is selected at 187, the first time interval T1 is reset and the time line starts over. A screen displaying patient and/or device information may be displayed or the previous active window may be displayed.

The end telemetry window may further include an "end session" field or button that allows a user to confirm that the session is over. A screen that allows the user to start a new session with a new patient may then be displayed.

Figure 5:
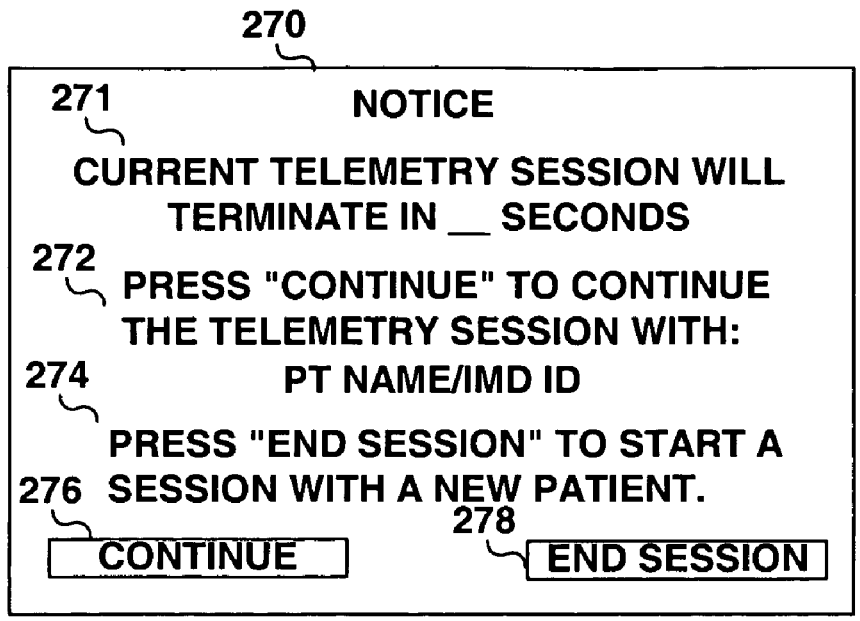
FIG. 5 is an illustration of a termination notification window that may be displayed on a graphical user interface of a programmer.

FIG. 5 is an illustration of a termination notification window that may be displayed on a graphical user interface of a programmer. The notification window 270 includes a notice field 271 indicating to the user that the current telemetry session is about to be ended or terminated. The notice field 271 may display the amount of time, e.g. the number of seconds, remaining in the T2 time interval until the telemetry link will be terminated.

The notification window 270 may further include a "continue" field 276 and an "end session" field 278 as described previously. User instruction fields 272 and 274 may indicate to the user what options he or she may take for continuing or ending the telemetry session. Instruction field 272 instructs the user to press the continue field 276 in order to continue the telemetry session with the current patient. The current patient may be indicated by name and/or by the IMD model or other identification number. If the continue field 276 is selected prior to expiration of T2, the telemetry link will not be terminated and the graphical user interface may return to a previously displayed window to allow the telemetry session to proceed.

Instruction field 274 instructs the user to press the end session field 278 in order to end the telemetry session with the current patient and allow a new session with a different patient to be initiated. If the end session field 278 is selected, the telemetry link may be terminated prior to expiration of T2 and a new window may be displayed indicating the current telemetry session has ended and allowing the user to start a new telemetry session with a new patient.

Figure 6:
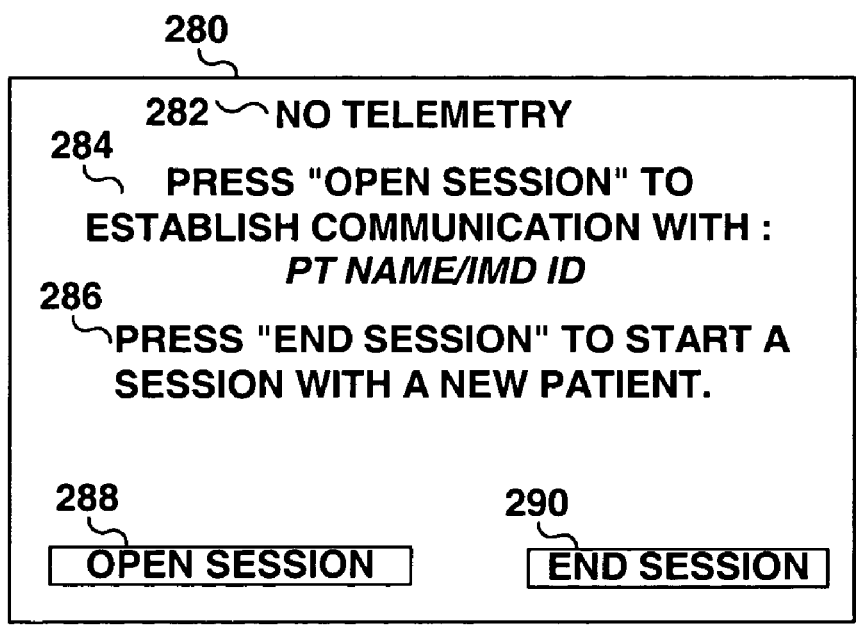
FIG. 6 is an illustration of an end session window that may be displayed on a graphical user interface of a programmer upon automatic telemetry termination.

FIG. 6 is an illustration of an end session window that may be displayed on a graphical user interface of a programmer upon automatic telemetry termination. End session window 280 includes a notification field 282 indicating no telemetry link is present between the programmer and an IMD. The end session window 280 may further include instruction fields 284 and 286. Instruction field 284 instructs the user to press an "open session" field 288 if the user would like to continue the telemetry session by re-establishing a telemetry link with the IMD of the current patient. The current patient may be identified by name in the end session window 280, and/or the IMD may be identified by model or serial number.

Instruction field 286 instructs the user to press the "end session" field 290 in order to confirm that the current telemetry session is over. A new window allowing the user to open a new telemetry session with a different patient may be subsequently displayed.

Figure 7:
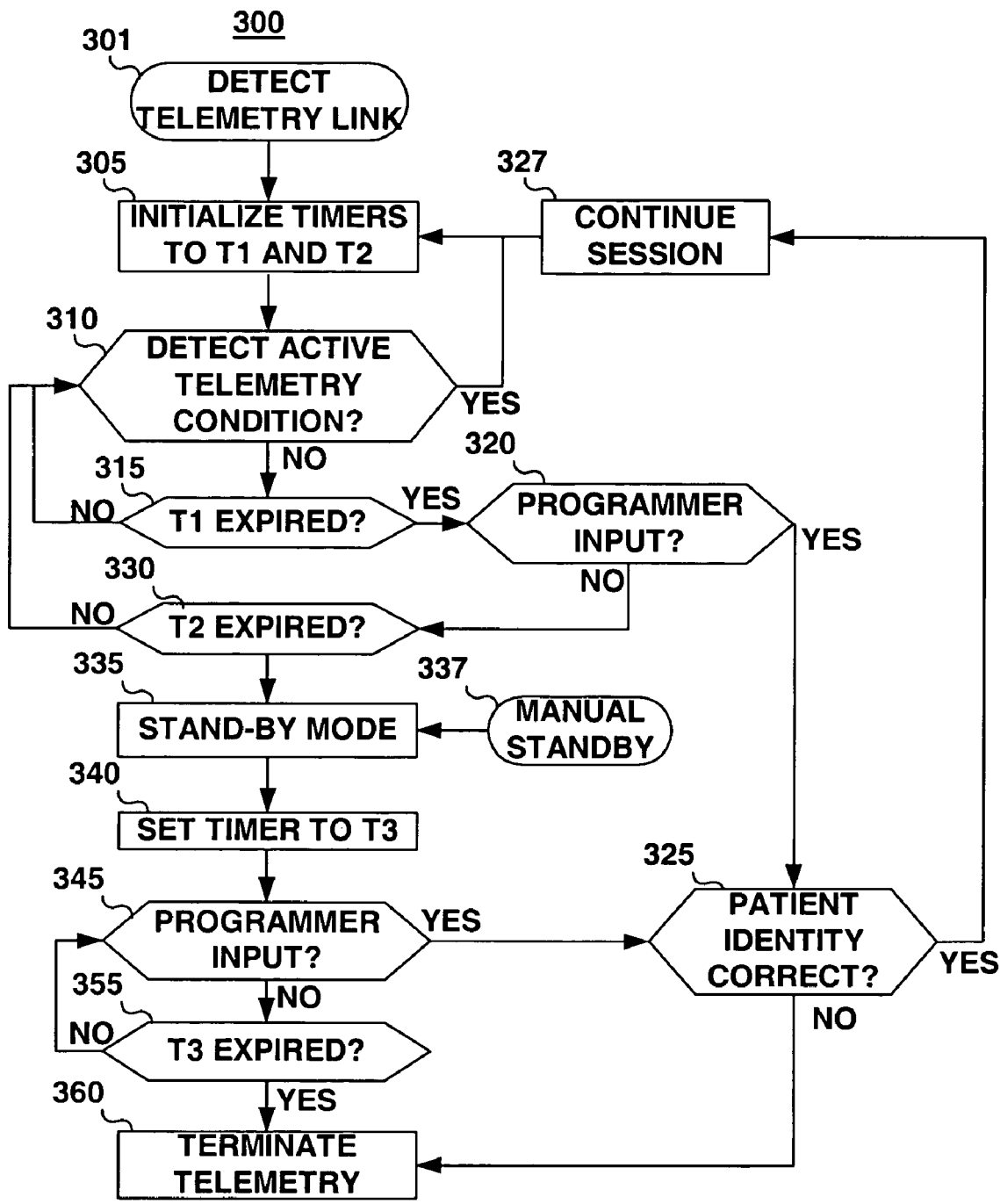
FIG. 7 is a flow chart of an alternative embodiment of a method for automatically controlling a telemetry link status.

FIG. 7 is a flow chart of an alternative embodiment of a method for automatically controlling a telemetry link status. Method 300 includes a "stand-by" mode in which the IMD telemetry circuitry is put into a low-output mode after a period of inactivity to maintain the telemetry link yet conserve power. Method 300 is initiated when a telemetry link is established between a programmer and IMD at step 301. At step 305, two timers are initialized to two different time intervals, T1 and T2. Monitoring for active telemetry session conditions begins at step 310. Active telemetry session conditions may be defined as described previously. If an active telemetry condition is detected prior to the expiration of timer T1, method 300 returns to step 305 to reset timers T1 and T2.

If the first time interval, T1, expires without detection of an active telemetry condition, as determined at decision step 315, and the programmer receives user input that would require programmer-IMD communication, as determined at decision step 320, the user is required to verify the patient and/or device identification at step 325. The type of user input received by the programmer requiring patient or device verification may be predefined. Typically user input that requires patient and/or device identity verification will be a programming or interrogation command, which result in programmer-IMD communication. Other types of user input that do not result in programmer-IMD communication, such as navigating through programming screens, may not require patient or device verification.

Before the programmer responds to the input received at decision step 320, the correct identification of the patient and/or associated IMD must be confirmed by the user to ensure that a programming or interrogation command is communicated to the intended patient and device. If the patient or IMD identity is incorrect, the telemetry link may be terminated at step 360. Telemetry link termination may occur immediately or at a future time and be executed automatically or manually through user selection. A user may then establish a new telemetry link with the intended IMD.

In an alternative embodiment, the telemetry link may remain established after a failed patient/device identity confirmation. Method 300 would proceed to step 330. If the second, T2, time interval has not expired, method 300 may continue monitoring for active telemetry conditions. If T2 expires, the high-output telemetry link is converted to a low-output, stand-by mode at step 335.

If the patient and device identity are correct, as confirmed at decision step 325, the telemetry session continues at step 327. The programmer responds appropriately to the input received at step 320. Method 300 then returns to step 305 to reset timers T1 and T2 and to continue monitoring for active telemetry session conditions.

The first time interval T1 is typically a shorter time interval than the second time interval T2. After expiration of T1, patient and/or IMD identity verification is required in order to continue a telemetry session. The high-output mode of the telemetry link is unchanged if the identity is correctly verified. If T1 expires (step 315) and no programmer input is received (step 320) but T2 has not yet expired, as determined at decision step 330, method 300 continues to monitor for active telemetry conditions at step 310, and the telemetry link remains in the high-output mode. However, if T2 expires (step 330) without detecting programmer input (step 320), the IMD telemetry circuitry is put into stand-by mode at step 335. The stand-by mode is a low-power, hand-shaking mode that maintains the telemetry link with the programmer but conserves IMD battery energy.

A user-selectable icon or button may be provided on the programmer user interface to allow the user to manually select a standby mode at any time during a programming session. If standby mode is selected manually as indicated by step 337, the telemetry link is converted to the standby mode at step 335.

A timer may be set to a third time interval T3 at step 340 at the start of the stand-by mode. If programmer input that requires programmer-IMD communication occurs at decision step 345 during the stand-by mode, patient and/or device identity is confirmed at step 325. After confirming the patient and/or device identity, the programmer responds to the programmer input, and the telemetry session continues at step 327. The IMD telemetry circuitry will be returned to a high-output mode for communicating with the programmer. If no programmer input is received prior to expiration of the T3 time interval, as determined at decision step 355, the telemetry link may be terminated at step 360 by putting the IMD telemetry circuitry to sleep. Alternatively, the IMD may remain in the stand-by mode set at step 335 until the telemetry link is terminated by a user-entered command or the patient leaves the telemetry range.

Figure 8:
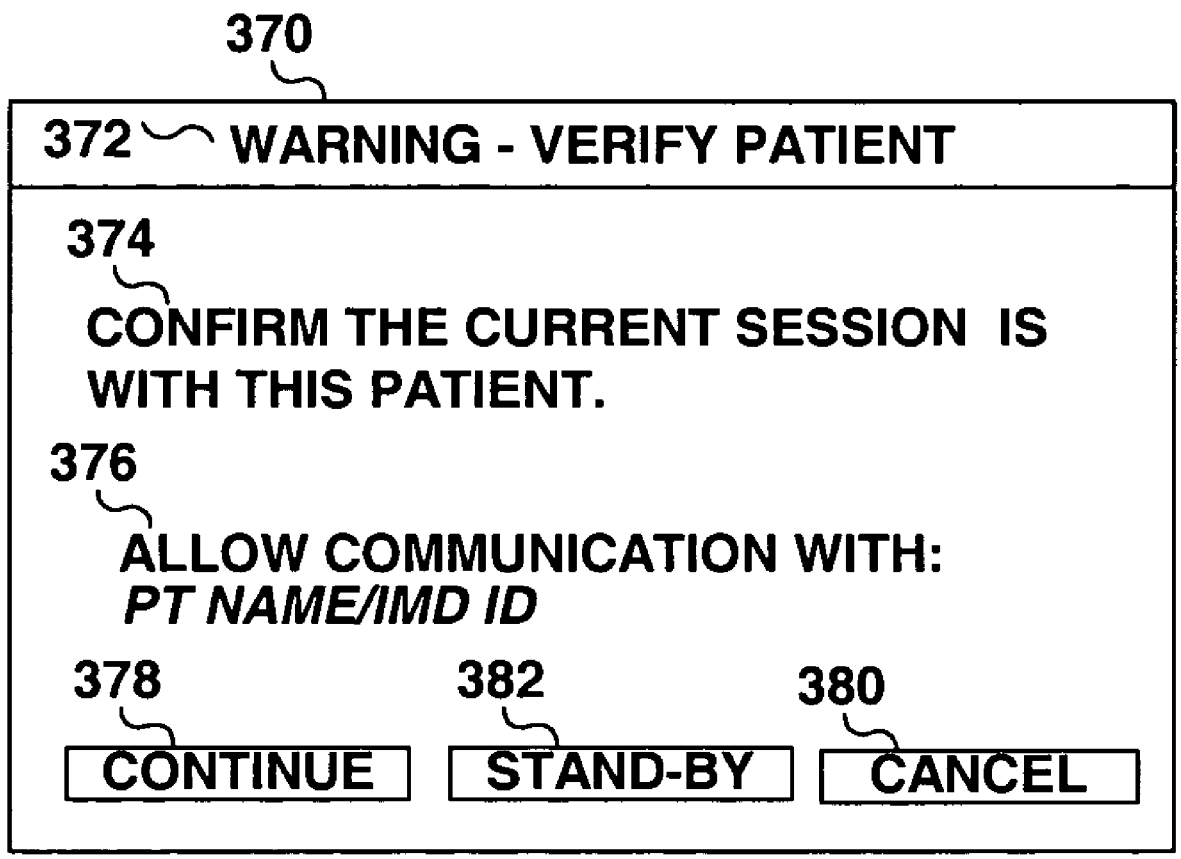
FIG. 8 is an illustration of a window for display on a graphical user interface for presenting patient identity verification information during a telemetry session.

FIG. 8 is an illustration of a window for display on a graphical user interface for presenting patient identity verification information. Window 370 may be displayed on a programmer after receiving user-input following a predetermined time interval during which no active telemetry conditions are detected. Window 370 includes a field 372 for warning the user that patient verification is required. Field 374 instructs the user to confirm that the programmer input is intended for the patient or device with which the programmer is currently communicating. Field 376 provides the identity of the patient and/or IMD. The user may select a "continue" field 378 to confirm that the communication may proceed with the identified patient or device. The user may select the "cancel" field 380 if the identified patient or IMD is not the intended IMD. A "cancel" input may automatically terminate the current telemetry link or may trigger a second window allowing the user to terminate the current telemetry link. A new telemetry link may then be established with the intended IMD.

An additional "stand-by" field 382 or equivalent icon may be provided in window 370 to allow a user to manually select to convert to a low-output stand-by mode. A stand-by field 382 or equivalent icon may be displayed on any of the windows described herein or any other available programming screens or windows to allow a clinician or user to put the IMD telemetry circuitry into stand-by mode at any time during a telemetry session. In this way, IMD battery life may be conserved during clinical or surgical procedures, unrelated interruptions, or other delays that may occur during a telemetry session. For example, during a patient follow-up session, IMD data may be retrieved. The patient may then be asked to exercise for a period of time after which new IMD data will be retrieved. The IMD may be selectively put into stand-by mode by the user during the period of exercise in order to conserve IMD battery energy.

Figure 9:
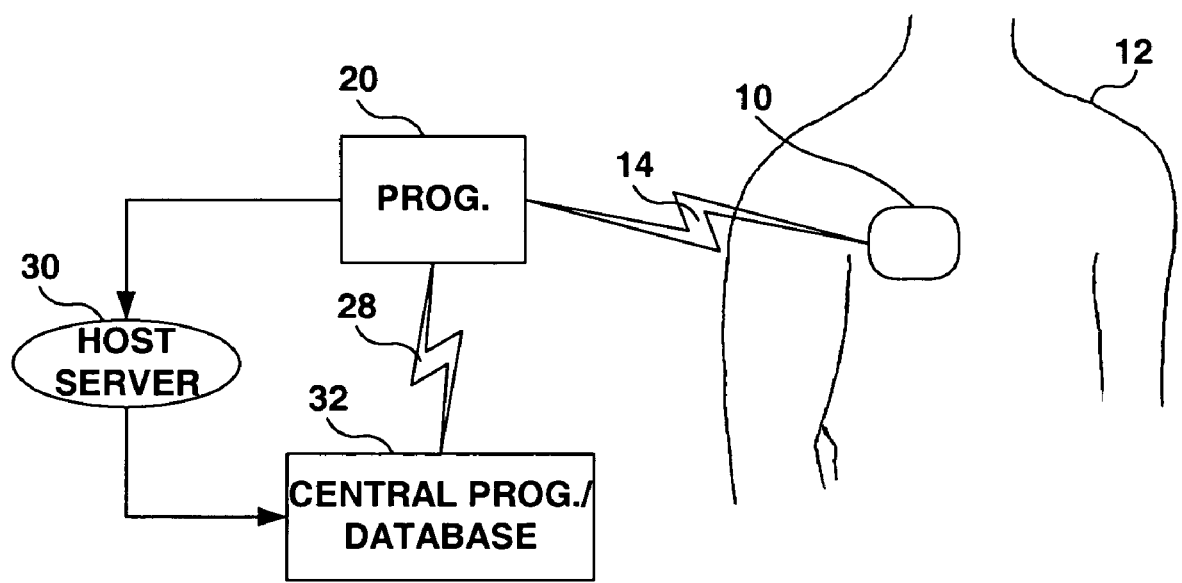
FIG. 9 is an illustration of a process for remote patient management.

FIG. 9 illustrates a general scheme by which remote patient management may be performed. Practice of the disclosed invention is not limited to local patient management procedures in which the patient having an IMD is in the presence of a clinician. The communication scheme shown in FIG. 9 enables clinical management of patients either in a hospital setting or in a home environment where the patient having the IMD is located remotely from a clinician using centralized patient management system. Programmer 20, which may be a programmer or home monitor, is located in the proximity of IMD 10, implanted in a patient 12, to allow telemetry link 14 to be established. Programmer 20 is coupled to a communication network 28 to allow data to be transferred between programmer 20 and a centralized patient management system that includes a central programmer and database 32. Data may be transferred between central programmer and database 32 and remote programmer 20 via a host server 30 which may perform data conversion operations and other data processing. Other examples of communication schemes that may be used in remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Central programmer and database 32 includes a database for storing medical records and programs or algorithms for analyzing and presenting medical data. Central programmer and database 32 may further include a processor for converting data to or from a device format. Alternatively, data conversion may be performed by host server 30. To facilitate programming operations, a graphical user interface may be used for viewing and selecting programming options and commands to be transferred to IMD 10 via remote programmer 20. Central programmer and database 32 may be implemented on a computer located at a clinic or may be implemented on the Internet, accessible using a web browser.

In accordance with the present invention, active telemetry session conditions may be monitored by control circuitry included in the remote patient management system. Such monitoring may be performed by the central programmer and database 32, the remote programmer 20, and/or IMD 10. Active telemetry session conditions may be monitored as described previously in conjunction with FIGS. 3A, 3B and 7. Active telemetry session conditions may include those described previously and further include conditions relating to data transfer between central programmer 32 and remote programmer 20 and/or conditions relating to user input received by central programmer 32.

Inactive telemetry session conditions and continuation conditions may also include conditions relating to data communications between central programmer 32 and remote programmer 20 and/or conditions relating to user input received by central programmer 32. As such, the methods described herein in conjunction with FIGS. 3A, 3B and 7 may be implemented in a remote patient management system. When a telemetry session is determined to be inactive for a specified period of time, telemetry link 14 established between the remote programmer 20 and IMD 10 may be terminated or converted to a low-output, stand-by mode as described previously. Additionally or alternatively, telemetry communication following a specified period of inactivity may be prohibited unless the patient and/or device identity are correctly verified as described in conjunction with FIG. 7. A patient alert signal may optionally be generated by IMD 10 if communication between remote programmer 20 and IMD 10 is attempted after a period of inactivity during a remote patient management session.

During remote patient management sessions, windows 270, 280, and 370 shown in FIGS. 5, 6 and 8, respectively, will be displayed by central programmer 32. User selections made in windows 270, 280, and 370 are communicated to the remote programmer 20 which responds accordingly in maintaining an active telemetry link, terminating the link, or converting the link to a stand-by mode.

Thus, a system and method that provides automatic monitoring and control over telemetry link status has been described. Automatic telemetry termination or conversion to a low-output, stand-by mode provides a safety measure for preventing unintended interrogation and programming of an IMD and for conserving IMD battery longevity. Patient safety is promoted by requiring patient and/or device identity verification prior to allowing programmer-IMD communication after a period inactivity. The various embodiments described herein are intended to be exemplary, not limiting, with respect to the following claims.

What is claimed is:

1. A method, comprising:
   detecting a predetermined condition evidencing an active telemetry session between an IMD and a programmer;
   setting a timer to a predetermined time interval whenever the predetermined condition is detected;
   initiating a telemetry termination operation if the timer expires prior to detecting a subsequent predetermined condition, the telemetry termination operation comprising;
   setting a timer to a second time interval;
   displaying a user notification message of an impending telemetry termination;
   initiating a low-output mode of IMD telemetry circuitry that maintains a low-output telemetry link between the IMD and the programmer; and
   terminating the telemetry link between the IMD and the programmer upon expiration of the second time interval.

2. The method of claim 1 wherein the telemetry termination operation further includes:
   detecting a telemetry continuation condition; and
   aborting the termination operation if a continuation event is detected prior to expiration of the second time interval.

3. The method of claim 1 further including generating a patient warning if a telemetry communication occurs after expiration of the timer.

4. An implantable medical device communication system, comprising:
   means for detecting an active telemetry session between an IMD and a programmer;
   means for resetting a timer to a predetermined time interval whenever the detecting means detects an active telemetry session;
   means for terminating the high-output mode of a telemetry link between the IMD and programmer when the predetermined time interval expires;

means for setting a second timer to a second predetermined time interval upon initiating a stand-by low-output telemetry link when said predetermined time interval of the first timer expires; and means for terminating the stand-by low-output telemetry link upon expiration of the predetermined second time interval.

5. The system of claim 4 wherein the means for terminating the high-output mode of the telemetry link includes means for initiating a low-output, stand-by telemetry link.

6. The system of claim 5 further including:
means for detecting a telemetry session continuation condition during the low-output telemetry link;
means for verifying the identity of an IMD upon detecting a telemetry session continuation condition;
means for converting the stand-by telemetry link back to the high-output telemetry link upon detection of a telemetry session continuation condition.

7. The system of claim 4 further including means for displaying a user notification message of the telemetry link status.

8. The system of claim 7 wherein the means for displaying a user notification message includes:
means for displaying a warning of a pending termination of a high-output telemetry mode;
means for displaying the remaining time until the high-output telemetry mode is terminated;
means for displaying a continue telemetry session command prompt; and
means responsive to continue command prompt input for canceling the high-output telemetry mode termination.

9. The system of claim 7 wherein the means for displaying a user notification message of the telemetry link status further includes:
means for displaying the identity of an IMD with which the programmer is currently or most recently in communication with;
means for confirming the IMD identity prior to allowing further communication between the programmer and IMD upon initiating a stand-by telemetry link when said first time interval expires; and
means for terminating the telemetry link between the IMD and the programmer if the IMD identity is not confirmed.

10. The system of claim 4 wherein means for detecting an active telemetry session includes means for detecting a near-field signal.

11. The system of claim 4 wherein means for detecting an active telemetry session includes means for detecting a telemetry signal strength.

12. The system of claim 4 wherein means for detecting an active telemetry session includes means for detecting an external monitoring signal.

13. The system of claim 4 wherein means for detecting an active telemetry session includes means for detecting patient movement.

14. A computer-readable medium containing instructions that when implemented in an IMD system cause the system to:
detect predetermined conditions evidencing an active telemetry session between the IMD and a programmer;
set a timer to a predetermined time interval in response to the detection of an active telemetry session condition;
terminate a high-output telemetry link between the IMD and the programmer upon expiration of the timer;
set a second timer to a second predetermined time interval initiate a stand-by low-output telemetry link when said predetermined time interval of the first timer expires; and
terminate the stand-by low-output telemetry link upon expiration of the predetermined second time interval.

15. The computer-readable medium of claim 14 containing instructions to further cause the system to:
display a message notifying a user of the status of the telemetry link.

16. The computer-readable medium of claim 14 containing instructions to further cause the system to:
detect a telemetry session continuation condition;
convert the low-output telemetry link to a high-output telemetry link if a telemetry session continuation condition is detected; and
terminate the low-output telemetry link if the timer expires before a telemetry session continuation condition is detected.

17. The computer-readable medium of claim 16 containing instructions to further cause the system to:
verify the IMD identity prior to converting the low-output telemetry link to a high-output telemetry link;
terminate the low-output telemetry link if the IMD identity is not verified.

18. The computer-readable medium of claim 14 containing instructions to further cause the system to:
set a second timer to a second time interval upon detection of an active telemetry condition;
verify the IMD identity prior to responding to input to the programmer if the second timer expires before an active telemetry condition is detected.

19. A method, comprising:
detecting a predetermined condition evidencing an active telemetry session between an implantable medical device (IMD) and a programmer;
setting a first timer to a first predetermined time interval and setting a second timer to a second predetermined time interval longer than the first predetermined time interval when the predetermined condition is detected;
maintaining a high-output mode of IMD telemetry circuitry during the first and second predetermined time intervals;
displaying a user instruction upon expiration of the first timer if the programmer receives user input during the second predetermined time interval that requires communication between the programmer and the IMD;
resetting the first timer to the first predetermined time interval and the second timer to the second predetermined time interval upon receiving user input in response to the displayed user instruction;
terminating the high-output mode of the IMD telemetry circuitry upon expiration of the second predetermined time interval; and
initiating a low-output mode of IMD telemetry circuitry that maintains a low-output telemetry link between the IMD and the programmer upon expiration of the second predetermined time interval.

20. The method of claim 19 wherein the user instruction comprises a verification of an identity of one of a patient and the IMD.

21. The method of claim 19 further comprising setting a third predetermined time interval upon initiating the low-output mode, and
terminating the low-output telemetry link upon expiration of the third predetermined time interval.

22. The method of claim 21 further comprising displaying the user instruction if the programmer receives user input requiring communication between the IMD and the programmer during the third time interval; and restoring the high-output mode upon receiving user input in response to the displayed user instruction.

23. The method of claim 19 wherein the low-output mode is a handshaking mode.

* * * * *